(12) United States Patent
Jahn et al.

(10) Patent No.: US 9,198,645 B2
(45) Date of Patent: Dec. 1, 2015

(54) CONTROLLED VESICLE SELF-ASSEMBLY IN CONTINUOUS TWO PHASE FLOW MICROFLUIDIC CHANNELS

(75) Inventors: Andreas Jahn, Gaithersburg, MD (US); Wyatt N. Vreeland, Washington, DC (US); Laurie E. Locascio, North Potomac, MD (US); Michael Gaitan, North Potomac, MD (US)

(73) Assignee: The United States of America, as represented by the Secretary of Commerce of The National Institute of Standards and Technology, Washington, DC (US)

( * ) Notice: Subject to any disclaimer, the term of this patent is extended or adjusted under 35 U.S.C. 154(b) by 2247 days.

(21) Appl. No.: 10/895,366

(22) Filed: Jul. 21, 2004

(65) Prior Publication Data

US 2005/0112184 A1 May 26, 2005

Related U.S. Application Data

(60) Provisional application No. 60/525,335, filed on Nov. 26, 2003.

(51) Int. Cl.
*A61K 9/127* (2006.01)
*A61B 17/00* (2006.01)

(52) U.S. Cl.
CPC ........... *A61B 17/0057* (2013.01); *A61K 9/1277* (2013.01); *A61B 2017/00654* (2013.01); *A61B 2017/00659* (2013.01); *A61B 2017/00898* (2013.01)

(58) Field of Classification Search
None
See application file for complete search history.

(56) References Cited

U.S. PATENT DOCUMENTS

| | | | |
|---|---|---|---|
| 6,454,945 B1 * | 9/2002 | Weigl et al. | 210/634 |
| 6,596,305 B1 * | 7/2003 | Edgerly-Plug | 424/450 |
| 2005/0032240 A1 * | 2/2005 | Lee et al. | 436/180 |

FOREIGN PATENT DOCUMENTS

CA WO 2004002453 * 1/2004

OTHER PUBLICATIONS

Paul et al. sciencemag.org vol. 285 Jul. 12, 1999.*
Chien et al. jornal of Chronmatography (924, (2001) 155-163.*
Anette et al. anal. Chem 2001, 73, 126-130.*
Andreas et al. Journal of Liposome research vol. 12, No. 3, pp. 259-270.*

* cited by examiner

*Primary Examiner* — Snigdha Maewall
(74) *Attorney, Agent, or Firm* — Millen, White, Zelano & Branigan, P.C.

(57) ABSTRACT

Methods for the formation of liposomes that encapsulate reagents in a continuous 2-phase flow microfluidic network with precision control of size, for example, from 100 nm to 300 nm, by manipulation of liquid flow rates are described. By creating a solvent-aqueous interfacial region in a microfluidic format that is homogenous and controllable on the length scale of a liposome, fine control of liposome size and polydispersity can be achieved.

16 Claims, 4 Drawing Sheets

CONTROLLED VESICLE SELF-ASSEMBLY IN CONTINUOUS TWO PHASE FLOW MICROFLUIDIC CHANNELS

This application claims priority to U.S. Provisional Application No. 60/525,335, filed Nov. 26, 2003.

Methods for the formation of liposomes that encapsulate reagents in a continuous 2-phase flow microfluidic network with precision control of size, for example, from 100 nm to 300 nm, by manipulation of liquid flow rates are described. By creating a solvent-aqueous interfacial region in a microfluidic format that is homogenous and controllable on the length scale of a liposome, fine control of liposome size and polydispersity can be achieved. Traditional liposome preparation methods are based on mixing of bulk phases, leading to inhomogeneous chemical and/or mechanical conditions during formation; hence liposomes prepared by those methods are often polydisperse in size and lamellarity.

There are a growing number of applications for nanoscale particles in biology that include interrogating (see, for example: E. J. Park, M. Brasuel, C. Behrend, *Anal. Chem.* 75, 3784 (2003); A. S. Arbab, L. A. Bashaw, B. R. Miller B R, *Transplantation* 76, 1123 (2003); M. E. Akerman, W. C. W. Chan, P. Laakkonen, *Proc. Natl. Acad. Sci. U.S.A.* 99, 12617 (2002); M. Bruchez, M. Moronne, P. Gin P, *Science* 281, 2013 (1998); W. C. W. Chan, S. M. Nie, *Science* 281, 2016 (1998); B. Dubertret, P. Skourides, D. J. Norris, *Science* 298, 1759 (2002)), perturbing (see, for example: H. E. Sparrer, A. Santoso, F. C. Szoka, *Science* 289, 595 (2000); and I. Koltover, T. Salditt, J. O. Radler, *Science* 281, 78 (1998)) and stimulating (see, for example: A. K. Salem, P. C. Searson, K. W. Leong, *Nat. Mater.* 2, 668 (2003)) the cellular environment. The design and production of nanometer scale objects, such as quantum dots, colloidal particles, and vesicles, can be accomplished in bulk either by chemical synthesis or self-assembly processes. In the cellular factory, chemical synthesis and self-assembly processes are exquisitely controlled by the closely-regulated local environment to ensure the reproducible production of nanometer-scale components such as proteins and vesicles. In bulk production methods, the local environment is not well controlled leading to significant chemical fluctuations, or electrical, mechanical perturbations that often result in inhomogeneous populations of nanoparticles.

Liposomes (see, e.g., A. D. Bangham, M. M. Standish, J. C. Watkins, *J. Mol. Biol.* 13, 238 (1965)) are one example of nanoparticles that have been used for a wide variety of biological applications including targeted drug delivery and DNA transfection (see, e.g.: G. Gregoriadis, *Liposome Technology Volume 3; Targeted Drug Delivery and Biological Interactions* (CRC Press, Boca Raton, 1983); and D. D. Lasic, D. Papahadjopoulos, *Science* 267, 1275 (1995)). Liposomes are cellular mimetics composed of a lipid bilayer membrane that encapsulates and sequesters species inside from species residing outside the membrane. Of critical importance to the successful implementation of liposomes in vivo is the ability to control the liposome size and size distribution, as size influences the clearance rate from the body and ultimately determines the drug dosage. Conventional modes of liposome preparation require the mixing of two or more phases, typically liquid-liquid or liquid-solid, resulting in the spontaneous self-assembly of the lipid mixture into a spherical bilayer membrane (see, e.g.: G. Gregoriadis, H. da Silva, A. T. Florence, *Int. J. Pharm.* 65, 235 (1990); F. C. Szoka, D. Papahadjopoulos, *Proc. Natl. Acad Sci. U.S.A.* 75, 4194 (1978); C. Pidgeon, S. McNeely, T. Schmidt, *Biochem.* 26, 17 (1987); H. Hauser, *Biochim. Biophys. Res. Commun.* 45, 1049 (1971); S. Batzri, E. D. Korn, *Biochem. Biophys. Acta.* 298, 1015 (1973); T. H. Fischer, D. D. Lasic, *Mol. Cryst. Liq. Cryst. Lett.* 102, 144 (1984); H. Kikuchi, H. Yamauchi, S. Hirota, *Chem. Pharm. Bull.* 39, 1522 (1991); A. Wagner, K. Uhl-Vorauer, G. Kreismayer, *J. Lip. Res.* 12, 259 (2002); T. S. Aurora, W. Li, H. Z. Cummins, *Biochimica et Biophysica Acta* 820, 250 (1985); P. L. Luisi, P. Walde, Giant Vesicles (John Wiley & Sons, Chichester, 2000)). These self-assembly processes typically occur in a system with a characteristic length on the order of centimeters, resulting in chemical and/or mechanical conditions that are highly heterogeneous on the length scale of a liposome. Thus, a given liposome may experience any one of many different sets of mechanical and chemical conditions during its self-assembly, often leading to liposome preparations with large polydispersity with respect to size and lamellarity.

To best mimic biological systems, it is desirable to create environments that are controllable on the dimension of the particle itself to elicit fine control of nanometer scale synthesis and self-assembly processes. As an aspect of the invention, it was discovered that several characteristics of microfluidic systems provide the ability to accomplish process control at this level. First, in these microfluidic systems, interfacial forces dominate and bulk inertial forces are typically negligible, leading to enhanced heat and diffusional mass transfer properties. Second, the laminar flow conditions in microfluidic channels can be used to create a well-defined and predictable interfacial region between two fluids. This characteristic has in fact been used to focus fluid streams hydrodynamically to submicrometer dimensional scales for rapid mixing (see, e.g., J. B. Knight, A. Vishwanath, J. P. Brody, *Phys. Rev. Lett.* 80, 3863 (1998)) and patterning (e.g.: P. J. A. Kenis. R. F. Ismagilov, G. M. Whitesides, *Science* 285, 83 (1999)). These properties of microfluidics allow control of chemical processes on nanometer length scales that were previously difficult to access experimentally.

According to the invention for the formation of liposomes in microfluidic systems, the characteristics of fluidic flow in a micrometer-scale channel can be used to precisely control the distribution of chemical conditions and mechanical forces so that they are constant on a length scale equivalent to that of a liposome. Hence, forming liposomes in a micrometer-scale flow field results in more homogenous conditions during liposome self-assembly and resultant liposome populations that are more uniform in size, hence of low polydispersity. Theoretical analysis of the laminar flow field engendered by microchannel flow when three microfluidic channels intersect show that the distribution of chemical species within the microfluidic network is constant and predictable (see, e.g., FIG. 1a, further discussed below).

Thus, the invention includes methods for producing a liposome-containing composition, which includes: providing a solvent stream of a composition of lipids or lipid-forming materials dissolved in a solvent through a central microchannel having a hydrodynamic diameter of 100 μm or less, preferably 70 μm or less; and impinging on said solvent stream through at least one side microchannel at least one aqueous stream of an aqueous composition which hydrodynamically focuses the solvent stream and forms a stream within the central microchannel having an interfacial region where the solvent stream and the at least one aqueous stream diffuse into each other to provide conditions such that liposomes self-assemble from the lipids or lipid-forming materials. In a preferred embodiment, at least two aqueous streams provided by at least two side microchannels, which at least partially oppose one another, impinge on the solvent stream to hydrodynamically focus it. More preferably, two aqueous streams provided by two side microchannels each at a 90° or less angle to the solvent stream, and opposite one another, impinge on the solvent stream to hydrodynamically focus it. However, other means of providing one or more side streams to focus the solvent stream and provide the interfacial region for liposome formation may be used.

For collection of the formed liposomes, it can be useful to provide, downstream of the region where the liposomes form, at least one side outlet microchannel for removing non-liposome materials from the central microchannel. The formed liposomes will flow in the central microchannel, typically as a tightly focused stream in the center area of the channel, owing to the low Reynold's number laminar flow typical of microfluidics and to the low diffusion coefficient of the formed liposomes. The outlet can be simply provided by one or more branching side microchannels. Material outside the diameter of the tightly focused stream of formed liposomes will be removed by such outlet channels facilitating isolation of a liposome suspension formed in the center of the central microchannel. In a preferred embodiment, non-liposome materials are removed from the central microchannel by two side outlet microchannels angled at 90° or more to the central microchannel and on opposite sides thereof. Other means for separating the formed liposomes can also be used.

Although any devices which provide the necessary microfluidics can be used to carry out the method, preferably, the device for carrying out the method is in the form of a silicon wafer containing the microchannels in the desired pattern to provide the central microchannel, side microchannels and outlet microchannels, as desired. Known photolithography techniques can be used to pattern microchannels in silicon materials. For example, the microchannels may be fabricated in the silicon chip with a transparent wafer, e.g., glass, cover using a two-step photolithography process in combination with an anisotropic wet-chemical etch (TMAH), followed by anodic bonding. In a first photolithographic step, through-holes for fluidic access to the device are patterned in the back of the silicon chip. In a second step, the microchannel pattern is formed on the front of the chip. After the patterning is complete, the silicon chips are cleaned, and a wet oxide layer (e.g., a 500 nm thick $SiO_2$ film) is grown on the surface. Finally, the channels are sealed by a covering using an anodic bonding technique: for example, a 0.5 mm thick borosilicate (Pyrex) wafer is brought into contact with the front of the silicon chip, and the silicon/Pyrex sandwich is heated to, e.g., 400° C., with an applied voltage. Modifications may be made to these photolithography, etching and anodic bonding methods according to the knowledge in these arts.

In one embodiment, the microchannels are formed in a material transparent on at least one side to allow observation of the microchannel, e.g., with the glass cover construction discussed above. This allows observation of the flow and liposome formation in the microchannels. For this purpose, it can be advantageous to provide a fluorescing material in the solvent stream and/or the aqueous streams to allow fluorescent observation and/or imaging of the liposome formation through the transparent cover.

The microchannels are preferably etched on the surface of a silicon wafer to a width and depth of 10 to 200 µm, more preferably 20 to 160 µm. The entire length of the central microchannel is preferably about 10 to 30 mm. The fluid through-holes are etched preferably of the same width as the microchannels or larger on the back-side of the wafer and aligned to the microchannel network for input and output ports. The dimensions of the entire silicon chip with cover device are preferably about 20 mm to 50 mm long and 15 mm to 30 mm wide with a thickness of 0.7 mm to 1 mm.

The flow of the solvent and aqueous streams through the device is preferably accomplished by pumping of the streams into the central and side microchannels, respectively. However, other fluid driving methods, such as electrically driven pumping could be used. In a preferred embodiment, pumping is accomplished by using gastight glass syringes interfaced to the microchannel network through capillary tubing and capillary connectors that are bonded to the fluid through-holes etched in the silicon wafer. Programmable syringe pumps can be used to control the fluid flow rates by computer, for example, using a LabVIEW software interface. Fine control of the respective flow rates is advantageous for providing fine control over the size of the resulting liposomes. Preferably, the central microchannel is provided with a flow rate of the solvent phase of about 1 to 12 mm/s and the side microchannels, when two are provided, of about 10 to 100 mm/s.

When the two liquid phases come into contact, the solvent phase and aqueous phase rapidly diffuse into one another. The flow rates of the solvent and aqueous streams can be adjusted to control the degree of hydrodynamic focusing and ultimately the liposome size. The lipids self-assemble where the concentration of the solvent phase containing the lipid or lipid-forming materials and the aqueous composition is at a critical condition where lipids are no longer soluble and thus self-assemble into liposomes. The formed liposomes remain in the center of the microchannel because: (i) liposomes formed along the interfacial region follow stream lines and are directed to collect at the center point in the channel; and (ii) at this point the solvent has diluted to a concentration where it can no longer solubilize any fraction of the lipid.

One can control the liposome size by altering the ratio of the flow rate in the side inlet channels compared to the center inlet channel. As the bulk liquid flow rate in the center channel downstream of the first cross increases, the magnitude of the shear stresses applied to the liposomes as they self assemble also increases. This results in a decrease in both the mean and range (polydispersity) of liposome diameter. Thus, by tuning of the flow rates in the microfluidic channels, the physical characteristics of the resultant liposome preparation can be readily controlled, for example, over the range of 100 nm to 300 nm diameter. Further, the liposome preparations are more monodisperse in size than liposomes prepared by traditional bulk methods. Although not intending to be bound by this theory, it is believed that this results from the precise control of the flow conditions that are achieved in the microchannel format. In bulk systems, as the solvent mixes into the aqueous phase, it does so in an uncontrolled fashion, resulting in different sections of solvent diluting to their critical concentration for lipid solubilization under different applied mechanical shear stresses. This heterogeneity results in different liposome sizes, hence a more polydisperse sample. However, by reducing the length scale of the fluidic system, and taking advantage of low Reynolds number, laminar flow in a microfluidic network facilitates more controlled fluidic mixing on the length scale of the liposome. Specifically, the solvent reaches its critical concentration under the same applied shear stress, resulting in a more monodisperse population of liposomes.

A useful characteristic of liposomes is their ability to encapsulate (or perhaps excapsulate) ionic molecules from a surrounding aqueous medium. Thus, the invention includes embodiments wherein a reagent is included in the composition of lipids or lipid-forming materials and/or in the aqueous composition and at least a portion of the reagent is encapsulated (or excapsulated) in the liposomes. Examples of reagents which may be encapsulated in liposomes as part of the above-described methods include small molecules (for example, drugs, fluorescent molecules, amino acids) and large molecules (for example, proteins, peptides, DNA and RNA).

The lipid or lipid-forming materials used in the central microchannel to carry out the invention include all known materials for liposome formation. Examples of useful materials include combinations of phospholipid molecules and cholesterol. Particularly preferred are combinations of dimyristoylphosphatidylcholine, cholesterol, and dicetylphosphate. These materials are provided in a solvent which will dissolve the lipid or lipid-forming materials. The solvent must also be water miscible in order to diffuse into the aqueous composition. Examples of useful solvents include alcohols, such as isopropanol, methanol or ethanol. The lipids or lipid-forming materials are preferably provided in the solvent in a concentration of approximately 10 mM.

The aqueous composition is preferably an aqueous buffer solution, particularly preferably a phosphate-buffered saline solution, phosphate buffer, TRIS buffer or HEPES buffer.

By changing the length scale of the fluidics in which lipids self assemble into liposomes and simultaneously manipulating both the length scale and the shear forces applied to the vesicles upon formation, the invention advantageously provides fine control of liposome size and homogeneity. Particularly, liposome-containing compositions with liposomes having a mean diameter from 100 nm to 300 nm and a size distribution of 15 to 20% can be produced using the described methods. Microfluidics allows adjustment of the flow fields precisely using the simple principle of hydrodynamic focusing. This is a fundamental change in the way in which liposome vesicles are formed, thus enabling the production of monodisperse populations without the need for subsequent processing steps to modify liposome size.

The liposome self-assembly method described here can be used to provide liposomes for applications in on-demand drug encapsulation and delivery and is readily scaled up using microfluidics with the development of multiplexed multichannel systems. We also predict that the synthesis and self-assembly of nanoscale particles for other applications in nanotechnology will also greatly benefit from adaptations of this approach.

The entire disclosure of all applications, patents and publications, cited herein and of U.S. Provisional Application No. 60/525,335, to which this application claims priority, is incorporated by reference herein.

BRIEF DESCRIPTION OF THE DRAWINGS

FIG. 3(a) is a white light image showing the hydrodynamic focusing of the isopoanol injected into the aqueous buffer and its diffusion downstream; 3(b) is a fluorescence micrograph of $DiIC_{18}$ exhibiting its confinement within the liposome stream which has a much lower diffusion constant than isoproponal; and 3(c) is a fluorescent micrograph of water soluble carboxyfluorescein dye in the aqueous stream.

FIG. 4(a) is a fluorescence image for $DiIC_{18}$ that exhibits intercolation of the dye into the lipid bilayer; and 4(b) is a fluorescence image for carboxyfluorescein (CF) that is encapsulated in the liposome's aqueous interior.

Figure 1:
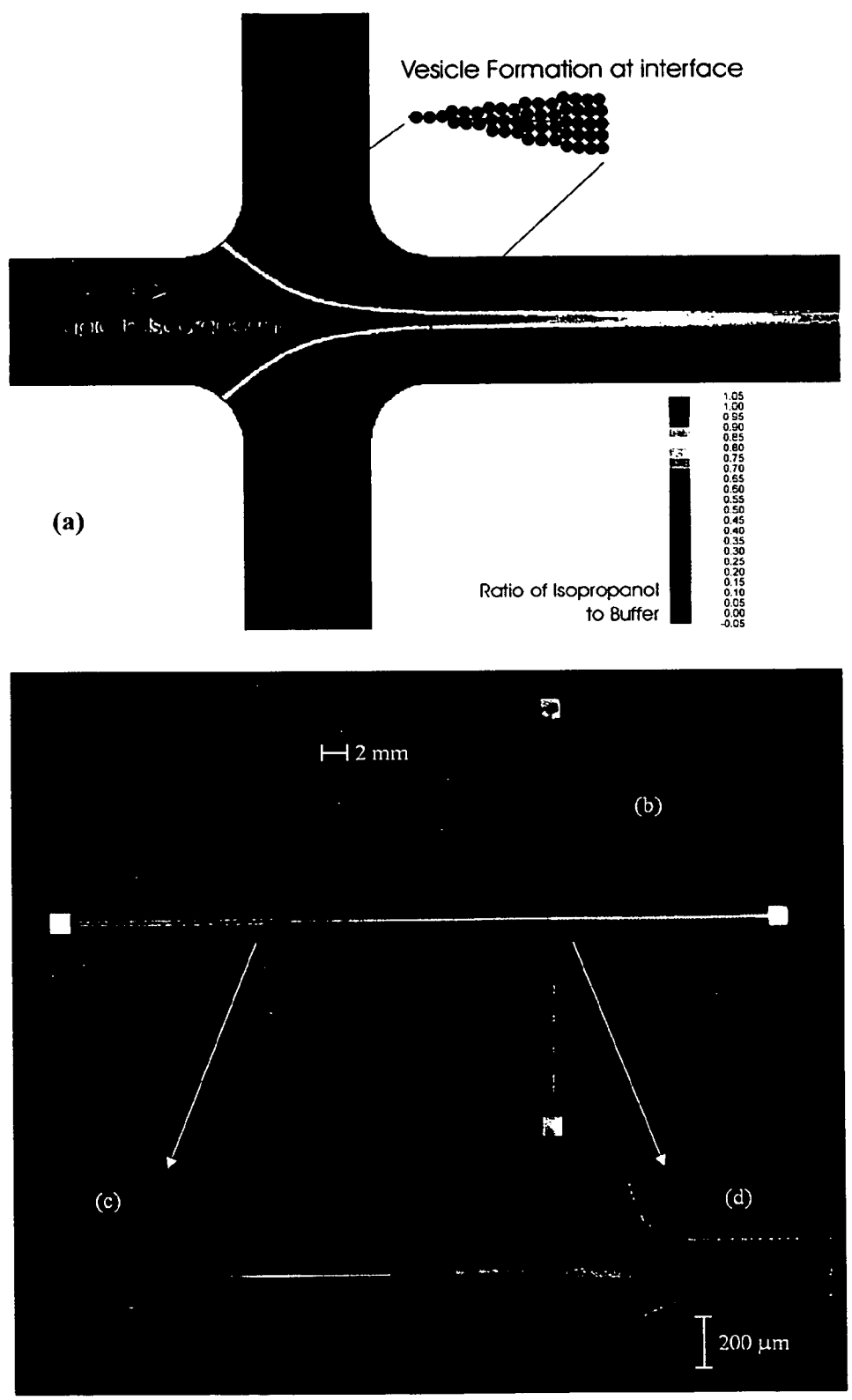
FIG. 1(a) provides a schematic of the self-assembly liposome formation process in a microfluidic channel. The color contours are generated by modeling of the flow field using Navier-Stokes convection and Stoke-Einstein diffusion analysis and represent the concentration ratio of isopropanol to the aqueous buffer. The lipid vesicles are formed where the concentration ratio of alcohol to buffer meets a critical condition when the lipids are no longer soluble in water, determined to be at 40 wt %.
FIG. 1(b) provides a fluorescence micrograph of a microchannel network with input streams on the left side and output streams on the right side.
FIG. 1(c) details the hydrodynamic focusing of the isopropanol stream at the first cross and FIG. 1(d) details the liposome collection and excess buffer extraction streams at the second cross.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

A stream of lipid tincture is hydrodynamically focused at a microchannel cross junction between two aqueous buffer streams each impinging on the lipid stream at 90°.

The lipid tincture contains dimyristoylphosphatidylcholine (DMPC) and cholesterol in a molar ratio of 1:1 diluted in chloroform solvent (all from Aldrich) with 1 wt % of 1,1'-dioctadecyl-3,3,3',3'-tetramethilindodicarbocyanine perchlorate ($DiIC_{18}$) added for fluorescent imaging. The chloroform solvent was evaporated under a stream of nitrogen at room temperature to form a lipid film on the bottom of a test tube. The test tube was then placed in a vacuum desiccator for at least 24 h to ensure dryness. The dried lipid mixture was resolubilized with 500 µL dry isopropanol yielding a 10 mM concentration of lipid solution.

To provide the microchannel cross junction, a microchannel network (200 µm channel width) was anisotropically etched on the surface of a silicon wafer (<100> orientation, 75 mm diameter, 0.3 mm thickness, from Virginia Semiconductor) to a depth of 40 µm through a photolithographically patterned thermal $SiO_2$ (100 nm) hard mask using tetraethylammonium hydroxide (TMAH, Alfa Aesar) (1:2 dilution 25% w/w aqueous TMAH solution, 80° C.). The same procedure was followed to etch fluid through-holes on the backside of the wafer that were aligned to the microchannel network in the front side. Following this, all surface oxide was removed (6% buffered HF etch) and then re-oxidized to form a 100 nm thick $SiO_2$ film encapsulating the silicon substrate. Finally, a glass cover wafer (75 mm diameter 0.1 mm thickness, Corning 7740) was anodically bonded to the front surface of the silicon wafer using a 580 V applied potential and heated to 400° C. to seal the microchannel network.

Following a procedure analogous to the bulk procedure that is described in L. Locascio-Brown, A. L. Plant, V. Horvath, *Anal. Chem.* 62, 2587 (1990), isopropyl alcohol containing the dissolved lipids is flowed through the center inlet channel, and an aqueous phosphate buffered saline solution flows through each of the two side inlet channels. Reagent transfers can be accomplished using gastight glass syringes interfaced to the microchannel network through capillary tubing (PEEK Tubing, Upchurch Scientific) and capillary connectors (Nanoports, Upchurch Scientific) that are bonded to the fluid through-holes etched in the silicon wafer. Programmable syringe pumps (Harvard Apparatus) can be used to control the fluid flow rates by computer, for example, using a LabVIEW software interface. Phosphate buffered saline solution (10 mM phosphate, 27 mM potassium chloride, 137 mM sodium chloride, pH=7.4) is used as the hydration buffer. For encapsulation experiments, a 1 mM carboxyfluorescein solution is prepared in this buffer. The liposome formulations (100 µL sample size) are collected at each flow condition in polycarbonate cuvets. After collection, 1 mL of phosphate buffered saline solution (10 mM) is added to each formulation and sealed for further characterization.

When the two liquid phases come into contact, the isopropanol rapidly diffuses into the aqueous phase and vice versa. The flow rates of the alcohol and buffer channels can be adjusted to control the degree of hydrodynamic focusing and ultimately the liposome size. The lipids self-assemble where the concentration of alcohol and buffer mixture is at a critical condition where lipids are no longer soluble and thus self-assemble into liposomes. Finite element modeling of this 2-phase flow process schematically presents the general approach to microfluidic self-assembly of liposomes in a microfluidic network (see FIG. 1a). A fluorescence image of the device used in these experiments is shown in FIG. 1b, with a close-up view in FIG. 1c of the hydrodynamically focused isopropanol stream where liposome formation occurs. Immediately downstream of the first cross intersection, the fluorescent intensity of the center stream increases sharply indicating the formation of the lipids into liposomes (the quantum efficiency of the fluorescent dye in this experiment ($DiIC_{18}$) increases dramatically upon incorporation into a lipid membrane). The liposomes then flow to the second cross intersection as a tightly focused stream owing to the low Reynold's number laminar flow typical of microfluidics and the low diffusion coefficient of liposomes. At this second cross (FIG. 1d) excess buffer is removed via the two side outlet channels and the liposome suspension is collected via the center outlet channel.

Figure 2:
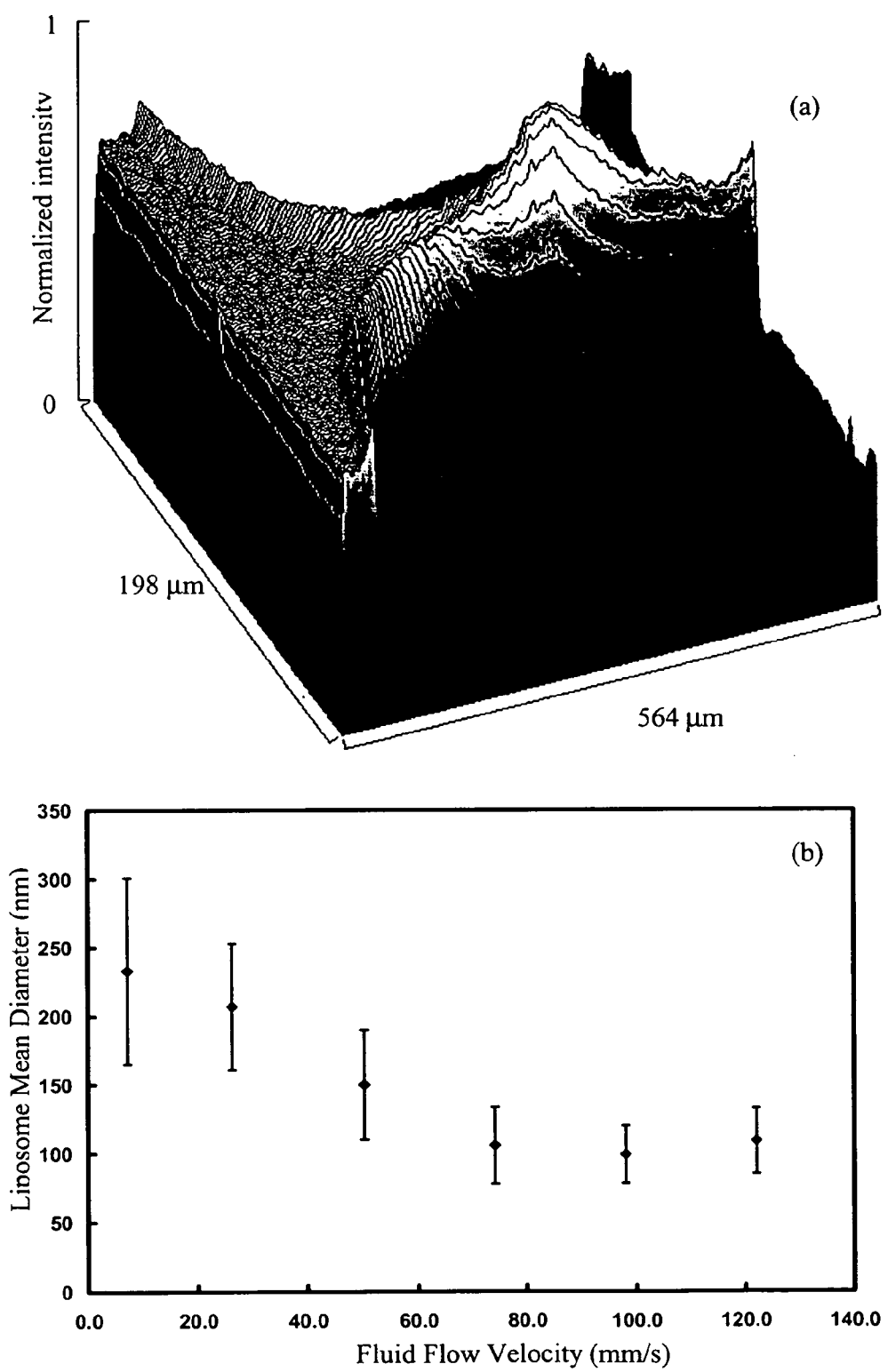
FIG. 2(a) shows a three-dimensional color contour map of the fluorescence intensity of $DiIC_{18}$ at the hydrodynamically focused injection region of liposome formation. The intensity exhibits a ridge of increased fluorescence at the alcohol-aqueous buffer interface owing to increased efficiency of $DiIC_{18}$ fluorescence efficiency due to intercolation of the dye into the lipid bilayer.
FIG. 2(b) shows the liposome mean diameter and standard deviation measured by light scattering vs. fluid flow velocity in center channel (The mean and standard deviation of the diameter of each of the liposome formulations is characterized by light scattering measurements (N4MD, Coulter Electronics Ltd.). For these measurements, a 0.1 wt % of Triton X-100 surfactant (Sigma) was added to the liposome formulations to reduce possible aggregation.) The isopropanol flow velocity is maintained at 2.4 mm/s while the flow velocity of each buffer channel is varied from 2.4 mm/s to 59.8 mm/s. The fluid flow velocity in the center channel on the x-axis is the sum of the flow velocities in each of the three input streams.

The liposomes form (as is manifested by the increased fluorescence of the $DiIC_{18}$) along the boundary between the isopropanol and water, as can be seen in FIG. 2a. A ridge of increased fluorescence is clearly visible as the aqueous streams focus the isopropanol. Fluorescence intensity increases to its maximum value immediately downstream of the minimum width of the isopropanol stream indicating the highest concentration of liposomes. Two effects lead to the high liposome concentration here in the system: (i) liposomes formed along the interfacial region follow stream lines and are directed to collect at the center point in the channel; and (ii) at this point the alcohol has diluted to a concentration where it can no longer solubilize any fraction of the lipid. According to two-dimensional modeling of this flow field with Navier-Stokes convection and Stoke-Einstein diffusion analysis, this increase in fluorescence intensity corresponds to an isopropanol concentration of approximately 40 wt %.

One can control the liposome size by altering the ratio of the flow rate in the side inlet channels compared to the center inlet channel. As the bulk liquid flow rate in the center channel downstream of the first cross increases, the magnitude of the shear stresses applied to the liposomes as they self assemble also increases. This results in a decrease in both the mean and range (polydispersity) of liposome diameter, as can be seen in FIG. 2b. Thus, by tuning of the flow rates in the microfluidic channel, the physical characteristics of the resultant liposome preparation can be readily controlled, for example, over the range of 100 nm to 300 nm. Further, the liposome preparations are more monodisperse in size than liposomes prepared by traditional bulk methods. Although not intending to be bound by this theory, it is believed that this results from the precise control of the flow conditions that are achieved in the microchannel format. In bulk systems, as the isopropanol mixes into the aqueous media, it does so in an uncontrolled fashion, resulting in different sections of alcohol diluting to their critical concentration for lipid solubilization under different applied mechanical shear stresses. This heterogeneity results in different liposome sizes, hence a more polydisperse sample (M. C. Woodle, D. Papahadjopoulos, *Meth. Enzymol.* 171, 193 (1989)). However, by reducing the length scale of the fluidic system, and taking advantage of low Reynolds number, laminar flow in a microfluidic network facilitates more controlled fluidic diffusion-based mixing on the length scale of the liposome. Specifically, the alcohol reaches its critical concentration under the same applied shear stress, resulting in a more monodisperse population of liposomes.

Figure 3:
FIG. 3 provides optical micrographs of the fluid flow fields for the liposome self-assembly process. Flow profiles are imaged in the microchannel network with a fluorescence microscope (Axioplan 2, Carl Zeiss) using a halogen lamp as an excitation source with appropriate filters for excitation and detection for $DiIC_{18}$ (excitation 540 nm±12.5 nm; beam splitter 565 nm; emission 605 nm±27.5 nm) and carboxyfluorescein (excitation 470 nm±20 nm; beam splitter 510 nm; emission 515 nm) and digitized using a CCD camera coupled to the top port of the microscope.

A useful characteristic of liposomes is their ability to encapsulate (or perhaps excapsulate) ionic molecules from a surrounding aqueous medium. Thus, functional characterization of liposomes self-assembled in a microfluidic channel is of interest. FIG. 3 shows three different images of the same microfluidic flow field. In panel (a), the microchannel network is viewed with transmitted light; immediately apparent is the visible refractive index change at the interface between the alcohol and aqueous phases that dissipates as the two phases interdiffuse. Panel (b) shows the microfluidic network under fluorescent imaging conditions appropriate to visualize $DiIC_{18}$ that is present as 1 wt % of the lipid fraction in the alcohol phase. The hydrodynamic focusing of this stream is clearly visible in this micrograph. It is also interesting that the $DiIC_{18}$ stream does not get progressively wider as the alcohol-aqueous boundary does as it migrates down the microchannel. This is due to the incorporation of the low molecular weight $DiIC_{18}$ into liposomes, which have a very low diffusion coefficient; and therefore diffuse minimally in the radial direction on the time frame of the liquid flowing through the microchannel. Panel (c) shows the microfluidic network under fluorescent imaging conditions appropriate to visualize carboxyfluorescein dye, which is present in the aqueous stream at a concentration of 1 mM. Here the aqueous streams can be seen focusing the alcohol stream. Careful inspection of this panel shows that the aqueous carboxyfluorescein dye does diffuse into the center region, showing that the carboxyfluorescein that is not encapsulated in liposomes still diffuses freely within the microfluidic channel.

Figure 4:
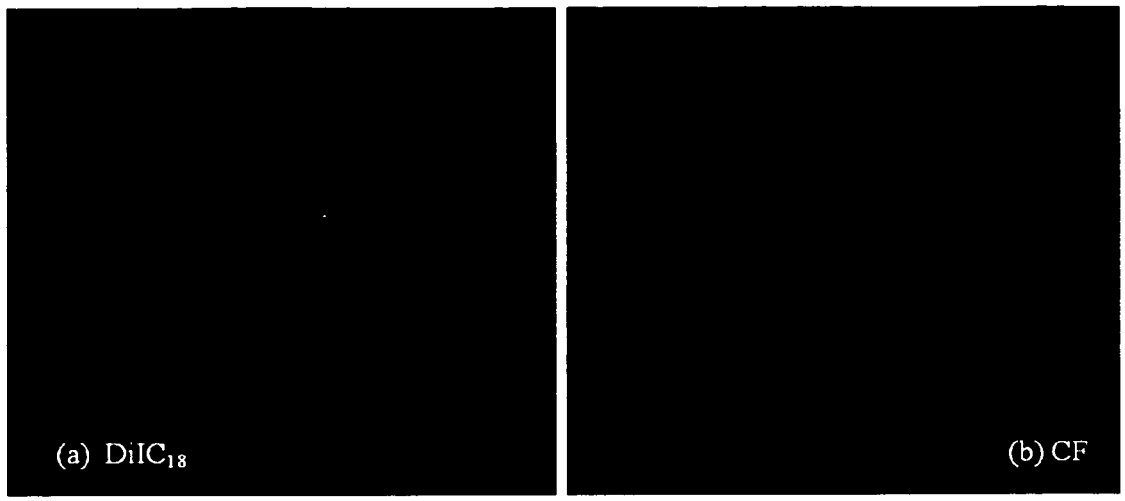
FIG. 4 provides two-color confocal fluorescence imaging of a single liposome formed in flow conditions of 0.5 µL/min flow rate of the isopropanol stream and 20 µL/min flow rate of the aqueous buffer streams. Two-color fluorescence imaging of liposomes showing analyte encapsulation were obtained using a confocal fluorescence imaging system (LSM 5 Pascal, Carl Zeiss) with a 40× objective and 10× digital zoom. The DiIC18 liposome image was measured with a laser excitation of 543 nm, through a 543 nm beam splitter, and emission was detected through a 560 nm low pass filter. The carboxyfluorescein liposome image was measured with a laser excitation of 488 nm passing through a 488 nm beam splitter, and emission was detected through a 530 nm low pass filter. The flow conditions in this example produce a liposome mean diameter of 133 nm and standard deviation of 26 nm determined by light scattering measurements.

Liposomes that self assemble in the microchannel presented in FIG. 3 should then have an aqueous interior that contains carboxyfluorescein surrounded by a lipid membrane with $DiIC_{18}$. Thus, two-color fluorescent imaging of a liposome should reveal the interior and membrane portions of the assembly. FIG. 4 shows a single liposome collected from this microfluidic flow network and nonspecifically adhered to a glass coverslip. Panel (a) shows the liposome with a fluorescence microscopy appropriate to visualize the $DiIC_{18}$ incorporated into the membrane, while panel (b) shows the same liposome visualized under the same magnification with fluorescence conditions to visualize carboxyfluorescein. The two images coincide in their spatial position and are stable over the time frame of several minutes as would be expected if the object in view is a contiguous membrane that encapsulates a continuous aqueous interior.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A method for producing a liposome-containing composition, which comprises:
   providing a solvent stream of a composition of lipids or lipid-forming materials dissolved in a water-miscible solvent through a central microchannel having a hydrodynamic diameter of 100 µm or less, and
   impinging on said solvent stream through at least one side microchannel at least one aqueous stream of an aqueous composition which hydrodynamically focuses the solvent stream and forms, under laminar flow conditions, a solvent stream and an aqueous stream within the central microchannel having an interfacial region between them where the solvent stream and the at least one aqueous stream diffuse into each other providing conditions where liposomes self-assemble from the lipids or lipid-forming materials to form a lipsome-containing composition with liposomes having a mean diameter of from 100 nm to 300 nm and a size distribution of 20% or less.

2. The method of claim 1, wherein a reagent is included in the composition of lipids or lipid-forming materials or in the aqueous composition or in both and at least a portion of said reagent is encapsulated in the liposomes.

3. The method of claim 1, wherein at least two aqueous streams are provided by at least two side microchannels, which at least partially oppose one another, and which impinge on the solvent stream to hydrodynamically focus it.

4. The method of claim 1, wherein two aqueous streams are provided by two side microchannels each at a 90° angle or less to the solvent stream, and opposite one another, which impinge on the solvent stream to hydrodynamically focus it.

5. The method of claim 1, wherein, downstream of the region where the liposomes form, non-liposome materials are removed from the central microchannel by at least one side outlet microchannel.

6. The method of claim 5, wherein non-liposome materials are removed from the central microchannel by two side outlet microchannels angled at 90° or more to the central microchannel and on opposite sides thereof.

7. The method of claim 1, wherein the lipid or lipid-forming materials are selected from: a combination of phospholipid molecules and cholesterol.

8. The method of claim 1, wherein the lipid or lipid-forming materials are selected from: a combination of dimyristoylphosphatidylcholine and cholesterol.

9. The method of claim 1, wherein the solvent is isopropanol, ethanol or methanol.

10. The method of claim 1, wherein the aqueous composition is an aqueous buffer solution.

11. The method of claim 1, wherein the aqueous composition is a phosphate-buffered saline solution, a phosphate buffer, a HEPES buffer, or a TRIS buffer.

12. The method of claim 1, wherein the microchannels are formed in a material transparent on at least one side to allow observation of the microchannel.

13. The method of claim 12, wherein a fluorescing material is provided in the solvent stream or in the aqueous stream to allow fluorescent observation of the liposome formulation or imaging of the liposome formation or both.

14. The method of claim 1, wherein the microchannels are formed in a silicon wafer.

15. The method of claim 1, wherein the solvent stream and aqueous stream(s) are pumped into the microchannels under computer-controlled flow rates.

16. The method of claim 1, wherein the resulting liposome-containing composition contains liposomes having a size distribution of 15 to 20%.

* * * * *